United States Patent
Valk et al.

(10) Patent No.: US 9,242,039 B2
(45) Date of Patent: Jan. 26, 2016

(54) SYSTEM AND METHOD FOR DIFFERENTIATING CONTAINERS IN MEDICATION DELIVERY

(75) Inventors: Jeffrey W. Valk, Dallas, TX (US); Timothy W. Valk, Boynton Beach, FL (US)

(73) Assignee: ADMETSYS CORPORATION, Boston, MA (US)

(*) Notice: Subject to any disclaimer, the term of this patent is extended or adjusted under 35 U.S.C. 154(b) by 738 days.

(21) Appl. No.: 13/395,605

(22) PCT Filed: Sep. 29, 2010

(86) PCT No.: PCT/US2010/050741
§ 371 (c)(1),
(2), (4) Date: Mar. 12, 2012

(87) PCT Pub. No.: WO2011/041429
PCT Pub. Date: Apr. 7, 2011

(65) Prior Publication Data
US 2012/0179132 A1    Jul. 12, 2012

Related U.S. Application Data

(60) Provisional application No. 61/246,813, filed on Sep. 29, 2009.

(51) Int. Cl.
*A61M 5/145* (2006.01)
*A61M 5/172* (2006.01)

(52) U.S. Cl.
CPC .......... *A61M 5/1452* (2013.01); *A61M 5/1723* (2013.01); *A61M 2205/3569* (2013.01);
(Continued)

(58) Field of Classification Search
CPC ............ A61M 5/1452; A61M 5/1723; A61M 2205/6045; A61M 2205/6072; A61M 2039/1005; A61M 2039/1022; A61M 2039/1044; A61M 2039/1077; A61M 2039/1083; A61M 39/1011; A61M 39/105; A61M 1/1008; A61M 3/2079; A61M 2205/3569; A61M 2205/3592; A61M 2205/6018; A61M 2205/6027

USPC .................................. 604/500, 151; 29/428
See application file for complete search history.

(56) References Cited

U.S. PATENT DOCUMENTS 4,055,175 A    10/1977  Clemens et al.
4,526,569 A     7/1985  Bernardi
(Continued)

FOREIGN PATENT DOCUMENTS

WO    WO 03-026558 A2    4/2003
WO    WO 03-047665 A1    6/2003
(Continued)

OTHER PUBLICATIONS

Extended European Search Report, regarding corresponding patent application EP 10821179.8 issued by the European Patent Office on Jun. 17, 2013, 7 pages.
(Continued)

*Primary Examiner* — Kami A Bosworth
*Assistant Examiner* — Brandy S Lee
(74) *Attorney, Agent, or Firm* — Barbara A. Wrigley; Oppenheimer Wolff & Donnelly LLP

(57) ABSTRACT

The present invention relates to a fluid delivery system that comprises a fluid container having a chamber structured to hold a fluid therein and a delivery device operable to control delivery of a fluid from the chamber of the fluid container. The fluid container includes a geometric mating member extending from an outer surface thereof. The delivery device includes a geometric mating receptacle structured to mate with at least a portion of the geometric mating member of the fluid container to verify compatibility of the fluid container with the delivery device. Alternatively or additionally, the fluid container may include a first data fixture component and the delivery device may include a second data fixture component that cooperates with the first data fixture component of the fluid container to verify compatibility of the fluid container with the delivery device.

22 Claims, 14 Drawing Sheets

(52) U.S. Cl.
CPC ............... *A61M2205/3592* (2013.01); *A61M 2205/6018* (2013.01); *A61M 2205/6027* (2013.01); *A61M 2205/6045* (2013.01); *A61M 2205/6072* (2013.01); *Y10T 29/49826* (2015.01)

(56) References Cited

U.S. PATENT DOCUMENTS

| | | | |
|---|---|---|---|
| 4,538,616 A | 9/1985 | Rogoff | |
| 4,633,878 A | 1/1987 | Bombardieri | |
| 5,080,653 A | 1/1992 | Voss et al. | |
| 5,109,866 A | 5/1992 | Guegan et al. | |
| 5,322,511 A * | 6/1994 | Armbruster et al. | 604/155 |
| 5,474,552 A | 12/1995 | Palti | |
| 5,630,706 A | 5/1997 | Yang | |
| 5,984,893 A | 11/1999 | Ward | |
| 6,017,318 A | 1/2000 | Gauthier et al. | |
| 6,056,734 A | 5/2000 | Jacobsen et al. | |
| 6,233,539 B1 | 5/2001 | Brown | |
| 6,544,212 B2 | 4/2003 | Galley et al. | |
| 6,572,542 B1 | 6/2003 | Houben et al. | |
| 6,740,072 B2 | 5/2004 | Starkweather et al. | |
| 6,743,202 B2 * | 6/2004 | Hirschman et al. | 604/131 |
| 6,958,053 B1 | 10/2005 | Reilly | |
| 6,966,880 B2 | 11/2005 | Boecker et al. | |
| 7,029,456 B2 | 4/2006 | Ware et al. | |
| 7,169,135 B2 * | 1/2007 | Duchon et al. | 604/246 |
| 7,204,823 B2 | 4/2007 | Estes et al. | |
| 7,367,942 B2 | 5/2008 | Grage et al. | |
| 7,491,187 B2 | 2/2009 | Van Den Berghe et al. | |
| 7,509,156 B2 | 3/2009 | Flanders | |
| 7,604,619 B2 | 10/2009 | Eich et al. | |
| 7,608,042 B2 | 10/2009 | Goldberger et al. | |
| 7,785,258 B2 | 8/2010 | Braig et al. | |
| 7,811,246 B2 | 10/2010 | Koops | |
| 7,811,279 B2 | 10/2010 | John | |
| 7,859,473 B2 | 12/2010 | Gibson | |
| 7,914,499 B2 | 3/2011 | Gonnelli et al. | |
| 8,121,857 B2 | 2/2012 | Galasso et al. | |
| 8,209,060 B2 | 6/2012 | Ledford | |
| 8,226,556 B2 | 7/2012 | Hayes et al. | |
| 8,273,052 B2 | 9/2012 | Damiano et al. | |
| 8,303,533 B2 | 11/2012 | Regittnig et al. | |
| 8,343,092 B2 | 1/2013 | Rush et al. | |
| 8,377,031 B2 | 2/2013 | Hayter et al. | |
| 8,388,598 B2 | 3/2013 | Steinkogler | |
| 8,425,417 B2 | 4/2013 | Leach et al. | |
| 8,449,524 B2 | 5/2013 | Braig et al. | |
| 2006/0235364 A1 * | 10/2006 | O'Hare et al. | 604/411 |
| 2007/0015972 A1 | 1/2007 | Wang et al. | |
| 2007/0088271 A1 | 4/2007 | Richards | |
| 2007/0106153 A1 * | 5/2007 | Neer et al. | 600/432 |
| 2007/0225675 A1 | 9/2007 | Robinson et al. | |
| 2008/0021294 A1 | 1/2008 | Levin et al. | |
| 2009/0069743 A1 | 3/2009 | Krishnamoorthy et al. | |
| 2009/0076383 A1 | 3/2009 | Toews et al. | |
| 2009/0112333 A1 * | 4/2009 | Sahai | 700/3 |
| 2009/0227989 A1 | 9/2009 | Burke et al. | |
| 2010/0057057 A1 | 3/2010 | Hayter et al. | |
| 2010/0137828 A1 | 6/2010 | Michard et al. | |
| 2010/0145173 A1 | 6/2010 | Alferness et al. | |
| 2010/0145303 A1 | 6/2010 | Yodfat et al. | |
| 2010/0174228 A1 | 7/2010 | Buckingham et al. | |
| 2010/0217238 A1 | 8/2010 | DeJournett | |
| 2010/0249561 A1 | 9/2010 | Patek et al. | |
| 2010/0262117 A1 | 10/2010 | Magni et al. | |
| 2010/0271213 A1 | 10/2010 | Krainz et al. | |
| 2010/0324382 A1 | 12/2010 | Cantwell et al. | |
| 2011/0021978 A1 | 1/2011 | Martin et al. | |
| 2011/0184266 A1 | 7/2011 | Levin | |
| 2011/0282320 A1 | 11/2011 | Steil et al. | |
| 2012/0071819 A1 | 3/2012 | Bruggemann et al. | |
| 2012/0123234 A1 | 5/2012 | Atlas et al. | |
| 2012/0179135 A1 | 7/2012 | Rinehart et al. | |
| 2012/0195182 A1 | 8/2012 | Pommereau et al. | |
| 2012/0275957 A1 | 11/2012 | Creaven et al. | |
| 2012/0330228 A1 | 12/2012 | Day et al. | |
| 2013/0165900 A1 | 6/2013 | Braig et al. | |
| 2013/0190674 A1 | 7/2013 | Case et al. | |

FOREIGN PATENT DOCUMENTS

| | | |
|---|---|---|
| WO | WO 2005/072792 A1 | 8/2005 |
| WO | WO 2007/051139 A2 | 5/2007 |
| WO | WO 2007/116226 A2 | 10/2007 |
| WO | WO 2008-033141 A1 | 3/2008 |
| WO | WO 2008/113772 A1 | 9/2008 |
| WO | WO 2013/032965 A1 | 3/2013 |

OTHER PUBLICATIONS

International Search Report, regarding International patent application Serial No. PCT/US10/50741, dated Nov. 23, 2010, 3 pgs.

* cited by examiner

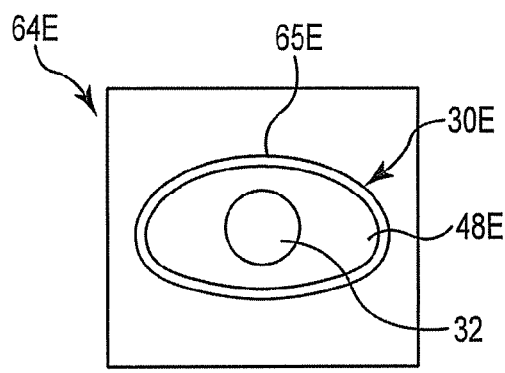
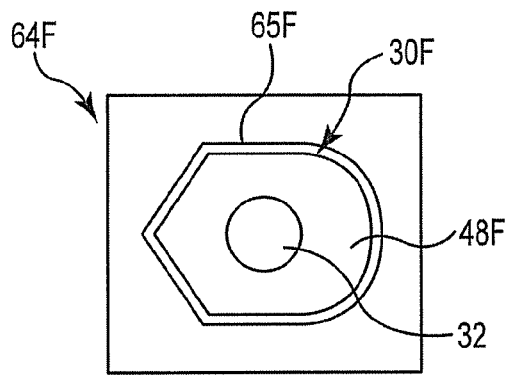
Fig. 7E        Fig. 7F
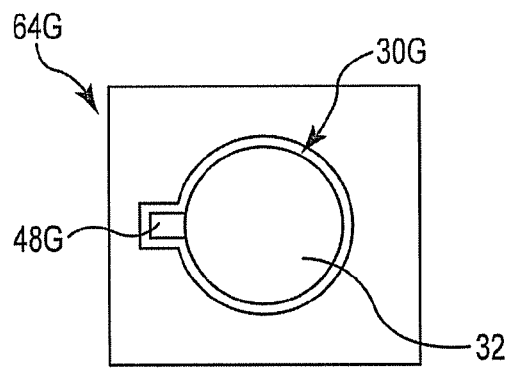
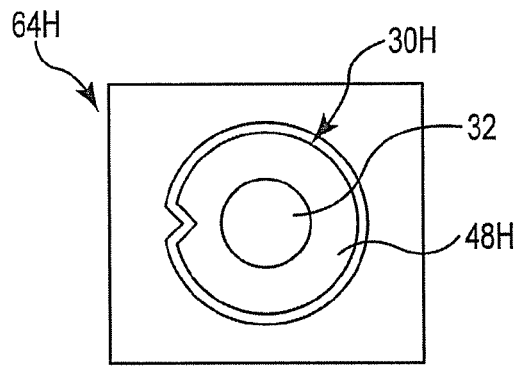
Fig. 7G        Fig. 7H
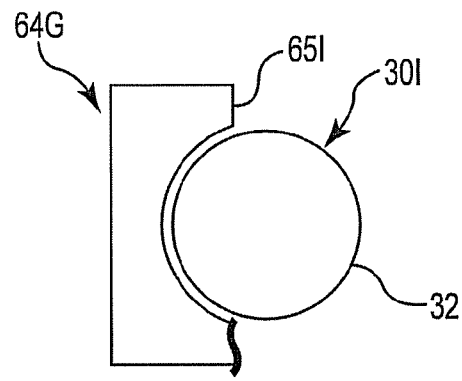
Fig. 7I

SYSTEM AND METHOD FOR DIFFERENTIATING CONTAINERS IN MEDICATION DELIVERY

FIELD OF THE INVENTION

The present invention relates to a system and method for differentiating syringes and other containers for dispensing medication that protects against delivery of incorrect medication and ensures compatibility of the dispensed medication with the delivery apparatus.

BACKGROUND OF THE INVENTION

Healthcare providers are often faced with treating patients for one type of physiological condition while monitoring at least one of a host of physiological parameters. It is often necessary to deliver various medications to patients in order to control these physiological parameters. Monitoring and controlling multiple physiological parameters for a plurality of patients requires a great deal of time and resources from healthcare providers. With ever increasing shortages in healthcare staff, workloads have been shown to be directly proportional to an increase in the occurrence of errors in medication delivery. Errors in medication delivery occur more frequently than commonly known and many of the errors are life threatening. In addition, these errors often go undiscovered and/or unreported.

Numerous physiological conditions are monitored in hospital care settings, including glycemic state, blood clotting, and the overall physiological stability of the patient. Typically, however, healthcare providers will measure only one physiological parameter, such as glucose level, prothrombin time, blood flow, hemoglobin level, heart rate, blood pressure, arterial oxygen concentration, or other cardiac output to treat the specific physiological condition under examination. Based on this measurement or a series of these measurements, the provider delivers medication to the patient in order to stabilize the physiological parameter and thus treat the physiological condition.

The control of glucose levels in seriously ill patients has proven to be a significant problem. Hyperglycemia is a frequent consequence of severe illness, occurring in both diabetic and non-diabetic patients, due to altered metabolic and hormonal systems, impaired gastrointestinal motility, altered cardiac function, increased catecholamine production, altered hepatic gluconeogenesis, relative insulin resistance, and increased corticosteroid levels. Symptoms associated with elevated levels of blood glucose include dehydration, weakness, greater risk of poor healing and infection, frequent urination, and thirst. Infusion of insulin has proven an effective method for treating hyperglycemia. However, insulin infusion without proper glucose level monitoring can lead to problems with hypoglycemia.

Visually distinguishing one medication from another can be difficult in many circumstances. Syringes and other containers have standardized sizes, and various liquid medications may look identical. Printed labels frequently become the only mechanism for determining that the medication installed in a pump or other delivery device is that intended. If a label is misread, health consequences to the patient can be severe.

The potential for error is compounded when a treatment application allows or requires delivery of multiple substances. The attending healthcare provider must then handle multiple potentially conflicting medications simultaneously, identifying and installing them without error. When this process is repeated frequently and for numerous patients, this burden of perfection becomes daunting.

One particularly sensitive application involves counterbalancing treatment. Such applications use opposing biologics in parallel to reinforce the body's innate "push-pull" mechanisms, raising or lowering certain biological levels as needed. Examples of this include regulation of serum glucose using insulin and glucose as mentioned above, vasodialation using a vasoconstrictor and vasodialator, and clotting using a coagulant and anticoagulant. Were opposing biologics to be reversed, such treatment could act to exacerbate imbalances in proportion to their magnitude, rather than correct them. This effect may be difficult to detect at small imbalance levels and escalate to a runaway effect, placing the patient in significant danger.

In addition to the considerable health hazards, errant medications can also be incompatible with delivery apparatuses. For example, a pump must exert a certain force on a fluid to displace an intended volume. A fluid with viscosity beyond expectation or pump tolerances could be dispensed in incorrect amounts and possibly damage the pump mechanism.

Thus, there exists a need for a physical system and method that acts to ensure that the medication container installed is that which is expected for the particular treatment application.

BRIEF SUMMARY OF THE INVENTION

The present invention addresses the foregoing problems by providing a fluid delivery system including a fluid container having a chamber structured to hold a fluid therein and a delivery device operable to control delivery of a fluid from the chamber of the fluid container. The fluid container includes a geometric mating member extending from an outer surface thereof. The delivery device includes a geometric mating receptacle structured to mate with at least a portion of the geometric mating member of the fluid container to verify compatibility of the fluid container with the delivery device.

In accordance with another aspect of the present invention, a fluid delivery system is provided that includes a fluid container having a chamber structured to hold a fluid therein and a delivery device operable to control delivery of a fluid from the chamber of the fluid container. The fluid container includes a first data fixture component associated therewith. The delivery device includes a second data fixture component associated therewith that cooperates with the first data fixture component of the fluid container to verify compatibility of the fluid container with the delivery device.

BRIEF DESCRIPTION OF THE DRAWINGS

FIGS. 7A-7I are diagrams illustrating exemplary differentiating geometries that may be used in accordance with the present invention.

DETAILED DESCRIPTION OF THE INVENTION

Generally speaking, the present invention is a system and method for differentiating syringes and other containers for dispensing medication that protects against delivery of incorrect medication and verifies compatibility of the dispensed medication with the delivery apparatus. As will be discussed in further detail to follow, the present invention applies to differentiation of infusion syringes and other medication containers by use of independent syringe geometries and counterpart receptacles on the syringe mounts or medication delivery devices. Alternatively or additionally, the present invention applies to differentiation of medication containers by use of data fixtures associated with the medication container and delivery device. One specific embodiment of the present invention applies to differentiation of medication containers in a multi-channel delivery environment.

Figure 1:
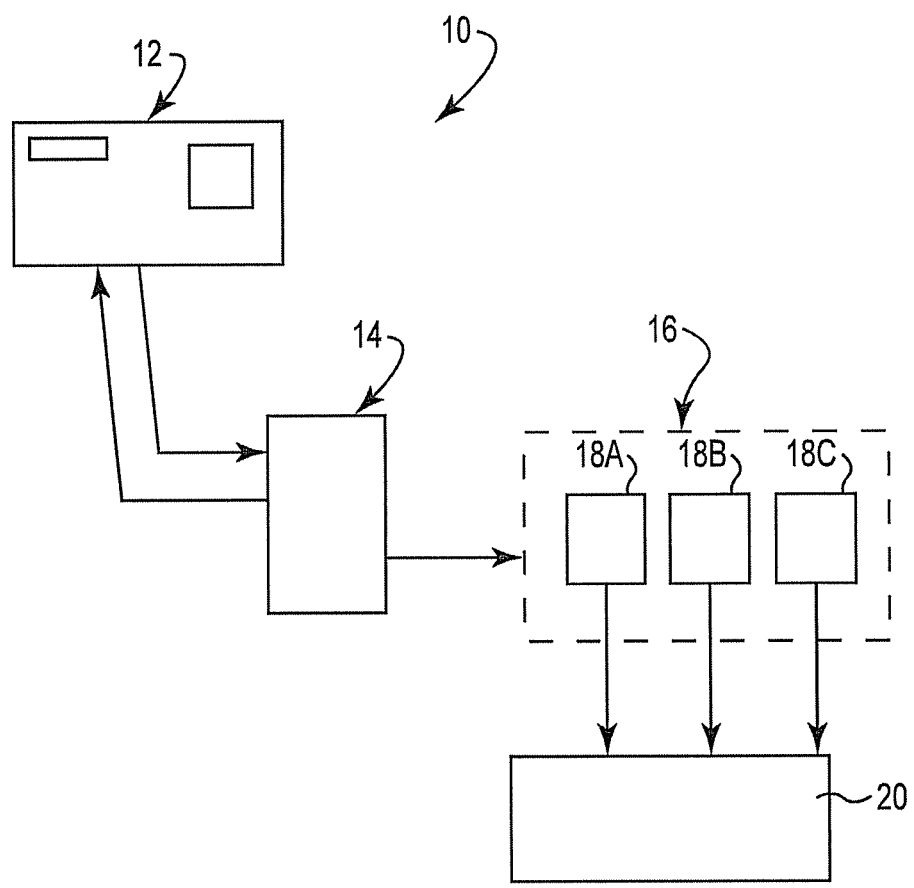
FIG. 1 is a block diagram illustrating one exemplary system for providing balanced, automated regulation of a physiological condition in a patient that utilizes the syringe differentiation system and method in accordance with the present invention.

FIG. 1 is a block diagram illustrating one exemplary system 10 for providing balanced, automated regulation of a physiological condition in a patient that utilizes the syringe differentiation system and method of the present invention. As illustrated in FIG. 1, the system 10 generally includes a physiological monitor 12, an electronic controller unit 14, and a delivery apparatus 16 including a single delivery channel or multiple delivery channels. Particularly, the delivery apparatus may include one or more delivery manifolds, pumps, or other suitable dispensing devices. In a multiple channel environment, the delivery apparatus may be configured with multiple single channel devices, one or more multiple channel devices, or a combination of single and multiple channel devices. The controller 14 may be separate from or integrated into the delivery apparatus 16.

In one exemplary embodiment, the delivery apparatus 16 includes two pumps, a first pump 18A and a second pump 18B for delivering medications to a patient 20. In an alternate embodiment, the delivery apparatus 16 may include one or more additional pumps, such as a third pump 18C, for delivery of one or more additional medications to the patient 20. As will be appreciated by those skilled in the art, the delivery apparatus 16 may include any number of pumps for the delivery of any number of medications. In the foregoing embodiments, the use of multiple pumps may allow for the concurrent monitoring and control of several physiological parameters and conditions.

Those skilled in the art will appreciate that pumps 18A, 18B, and 18C may be selected from a wide variety of infusion pumps commonly used in the medical industry including continuous and/or intermittent pumps, the selection of which will vary depending on criteria such as desired flow rates and/or delivery of large or small volumes. Infusion pumps can administer fluids in ways that would be impracticably expensive or unreliable if performed manually by healthcare providers. For example, the pumps can administer injections as little as 0.1 mL per hour (too small for a drip), injections every minute, injections with repeated boluses, up to a maximum number per hour, or fluids whose volumes vary by the time of day.

In one exemplary embodiment, the pumps 18A, 18B, and 18C are each structured to receive a syringe containing a medication for delivery to the patient 20. In this embodiment, the pumps are provided with a signal related to the desired volume of each medication to be delivered from the syringe to the patient. The pumps 18A, 18B, and 18C may be run with constant or variable speed drives for controlling the volume of medication delivered to the patient and the rate at which the medication is delivered. Data related to the delivery volume and rate may be stored by the controller 14. Thus, the delivery apparatus 16 is operable to provide controlled delivery of a first medication with the first pump 18A, a second medication with the second pump 18B, and a third medication with the third pump 18C as determined by the controller 14. The controller 14 may accept input from a single device or a range of devices which provides data point information about a primary physiological condition and, optionally, data point information about additional physiological conditions. The controller 14 may further be provided with adaptive logic for gradual, optimized, stabilization of one or more physiological conditions of the patient.

Those skilled in the art will appreciate that the system 10 may be structured as a stationary system used in intensive care units or emergency rooms in hospitals; a portable unit for use by emergency medical technicians such as in ambulances, at the scene of accidents, or when responding to other emergency situations; or a portable unit for use in the day-to-day care of ambulatory and non-hospitalized individuals. Thus, the "user" of the system may be a healthcare provider or the patient himself. Those skilled in the art will also appreciate that the system 10 may alternately include a miniature chip as the controller 14, wherein the chip can be operably connected to a means for encapsulating the medications being administered such that the encapsulated medications can be implanted in the patient's body and released on-demand based on an output signal from the controller.

Although the delivery apparatus 16 of system 10 has been described as delivering medication from syringes, the delivery apparatus 16 may be operable to deliver medication from any type of medication storage container. Thus, syringes are described merely for purposes of example and not limitation.

The system 10 is also described as including a physiological monitor 12 operably coupled to the controller 14 merely for purposes of example and not limitation. In various other embodiments, delivery of the medication may be performed under the direction of the attending healthcare provider and independent of an integrated physiological monitor.

As previously discussed, errors in medication delivery place the patient at risk of serious injury or death, and the potential for error is compounded when a treatment application allows or requires delivery of multiple medications. This is especially true when the attending healthcare provider must simultaneously identify, handle, and install multiple potentially conflicting medications, such as during a "counterbalancing" treatment. In addition to the considerable health hazards, errant medications can also be incompatible with a particular delivery apparatus. Thus, in order to address the foregoing risks, the storage container and delivery apparatus may include a differentiation means that protects against the delivery of incorrect medication and preserves compatibility of the dispensed medication with the delivery apparatus. It will be obvious to those skilled in the art that the differentiation means may be adapted for use with any type of medication storage container without departing from the intended scope of the present invention.

Figure 2A:
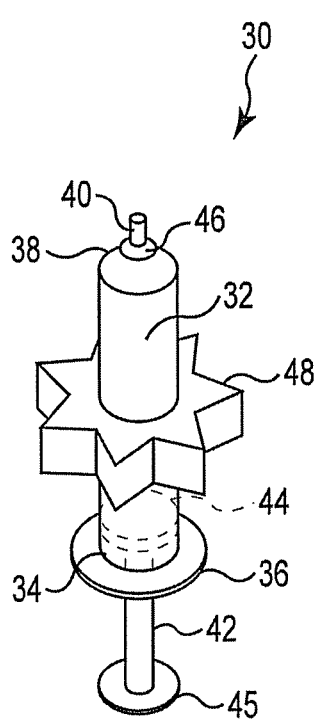
FIGS. 2A and 2B are perspective views illustrating one exemplary syringe that may incorporate a geometric differentiating means in accordance with the present invention.

FIG. 2A is a perspective view illustrating one exemplary syringe 30 that may incorporate a differentiation means in accordance with the present invention. As shown in FIG. 2A, the syringe 30 generally includes a cylindrical barrel 32 having a larger first end 34 with an outwardly extending flange 36 and a smaller second end 38 with a suitable connector 40, such as a luer connector, for engagement with the delivery apparatus. The flange 36 typically, but not necessarily, extends substantially perpendicular to the outer surface of the cylindrical barrel. The barrel 32 defines an internal chamber for storing a fluid medication.

As will be appreciated by those skilled in the art, the syringe 30 may be used either manually by a healthcare provider or in an automated delivery apparatus. In manual use of the syringe 30, the barrel 32 may be held between the first two fingers of the healthcare provider's hand with the outwardly extending flange 36 preventing the syringe from sliding between those two fingers. In automated use, the syringe 30 may be operably coupled to a suitable delivery device as will be illustrated in further detail in FIG. 3.

A plunger rod 42 is attached at its forward end to a suitable plunger member 44 that is sized and structured to prevent any leakage of medication through the first end 36 of the barrel 32. A circular rim 45 extends from the opposite end of the plunger rod 42 and provides a surface for exerting an actuation force on the plunger 44 to dispense the medication contained within the barrel 32. A suitable sealing element 46, such as a rubber stopper, may be disposed within the barrel 32 adjacent to the second end 38 to prevent unintentional leakage through the connector 40. In one exemplary embodiment, the sealing element 46 is pierced with a needle upon insertion of the syringe 30 into the delivery device.

The syringe 30 is illustrated in FIG. 2A as a conventional design employing a cylindrical barrel and a plunger merely for purposes of example. Those skilled in the art will appreciate that numerous other designs for medication containers that deliver medication when subjected to positive pressure are also possible. One example of such an alternative container design is a flexible container, such as a flexible bag or bulb, which is pressurized in use by a cooperating pump to drive medication from the container.

With further reference to FIG. 2A, a differentiation means in the form of a geometric mating member 48 extends outwardly from at least a portion of the barrel 32. The geometric mating member 48 allows for the identification of the syringe 30 to protect against delivery of incorrect medication and ensure compatibility of the dispensed medication with the delivery device. Additional details of this differentiation means will be provided below.

As will be appreciated by those skilled in the art, the geometric mating member 48 may be a separate component that is permanently coupled to the barrel 32 of the syringe 30 or other medication container. Coupling of the mating member 48 to the barrel 32 may be accomplished using any suitable means including, but not limited to, heat welding, an adhesive, or the like. Alternatively, the geometric mating member 48 may be manufactured as integral with the barrel 32 rather than modifying a "standard" syringe with the geometric member. When formed integral with the barrel 32, the internal geometry of the chamber may remain the same (e.g. cylindrical), thus manufacturing only the outer portion of the barrel differently, or may take on the geometry of the mating member.

Figure 2B:
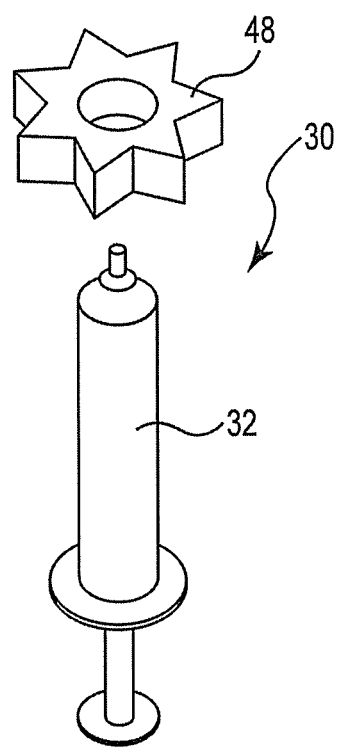

In yet another embodiment, adaptation of the syringe or other medication container may be temporary such that the geometric mating member 48 is removable from the syringe barrel 32 as illustrated in FIG. 2B. In this embodiment, the geometric mating member 48 may be removably coupled to the syringe 30 in any suitable manner including, but not limited to, a compression fit, a non-permanent adhesive, or the like. One advantage of providing a geometric differentiating member that is removable from the container is the ability to reuse the geometric differentiating member on another medication container in the future.

While FIGS. 2A and 2B depict the geometric differentiating member as applied to the barrel of a syringe, the geometric differentiating member may be applied to any suitable portion of a container, with a counterpart receptacle being applied in kind to the counterpart component on a delivery apparatus as will be discussed in further detail to follow. Examples may include positioning geometric differentiating members on the plunger or needle hub of a syringe. Additionally, numerous geometric differentiating members may be applied to a single syringe or container, thereby providing redundancy for further safety and compatibility assurance.

Figure 3:
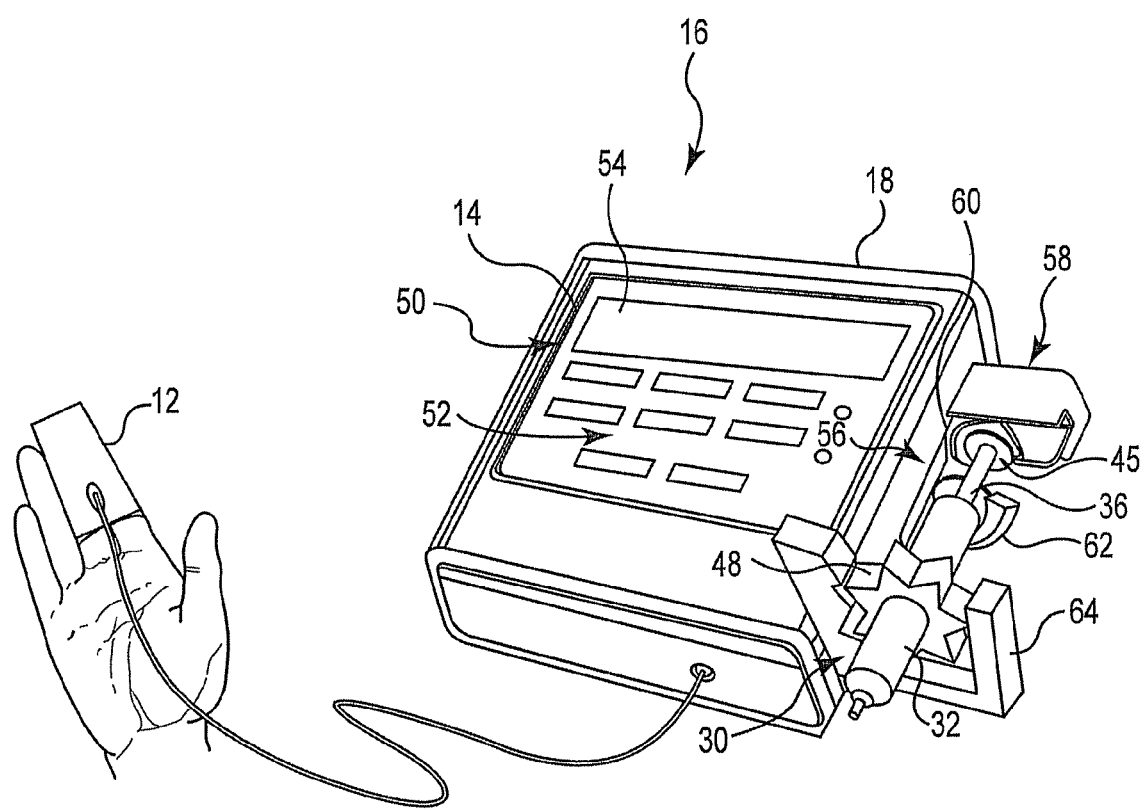
FIG. 3 is a perspective view of the syringe of FIG. 2 operably coupled to one exemplary infusion pump.

FIG. 3 is a perspective view of the syringe 30 of FIGS. 2A and 2B operably coupled to one exemplary delivery apparatus 16 including a pump 18 for dispensing medication from the syringe 30 based upon measurements input from a physiological monitor 12. As illustrated in FIG. 3, the pump 18 includes the controller 14 described above with reference to FIG. 1 incorporated therein. However, it should be understood that the controller 14 may alternatively be provided as a separate component that is operably coupled to the delivery apparatus 16.

The delivery apparatus 16 will be described with reference to a single channel pump that is operable to deliver medication from a single syringe for purposes of simplicity. However, it will be obvious to those skilled in the art that the teachings of the present invention may be extended to systems having more than one delivery channel or pump.

As illustrated in FIG. 3, the controller 14 includes control means 50 including a microprocessor within the body of the syringe pump 18 and an associated keyboard 52 and display 54. Various other switches, indicators, input devices, and the like may be provided on the body of the syringe pump 18 as will be apparent to those skilled in the art and which are not shown here in detail.

The pump 18 includes a delivery channel 56 extending along a side surface thereof that is structured to receive the syringe 30. Particularly, the delivery channel 56 includes a pump motor 58, a pump slide 60, a stop member 62, and a geometric mating receptacle 64. As generally illustrated in FIG. 3, the geometric mating receptacle 64 is structured to mate with a compatible geometric mating member, such as the geometric mating member 48, in order to protect against delivery of incorrect medication and ensure compatibility of the dispensed medication with the syringe pump 18. When the geometric mating member 48 is properly mated with the mating receptacle 64, the outwardly extending flange 36 abuts the stop member 62 to prevent axial movement of the syringe 30 in the forward direction. Furthermore, the circular rim 45 extending from the rearward end of the plunger rod 42 is received by the pump slide 60. The pump motor 58 is operable to drive the pump slide 60 in the axial direction, which in turn actuates the plunger 44 for controlled delivery of the medication contained within the barrel 32.

The pump motor 58, including the pump slide 60 for actuating the plunger rod 42 and plunger 44, may be operated by the controller 14 upon verification that the syringe 30 is the correct syringe containing the proper medication. The controller 14 may control numerous parameters including, but not limited to, delivery volume, delivery rate, delivery duration, or the like.

As will be appreciated by those skilled in the art, the delivery apparatus illustrated in FIG. 3 represents only one exemplary type of delivery apparatus that may be operable with the syringe differentiation means in accordance with the present invention and is presented merely for purposes of example and not limitation. Thus, geometric mating receptacles may be incorporated into any suitable delivery apparatus without departing from the intended scope of the present invention.

Figure 4A:
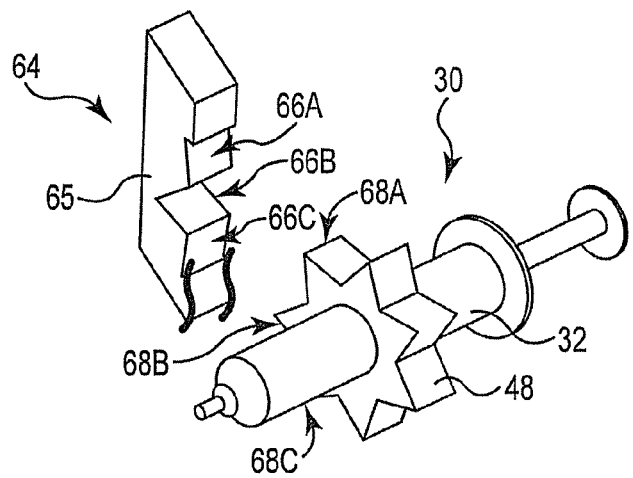
FIGS. 4A-4C are diagrams illustrating the mating relationship between a geometric mating member and a corresponding geometric mating receptacle in accordance with the present invention.
Figure 4B:
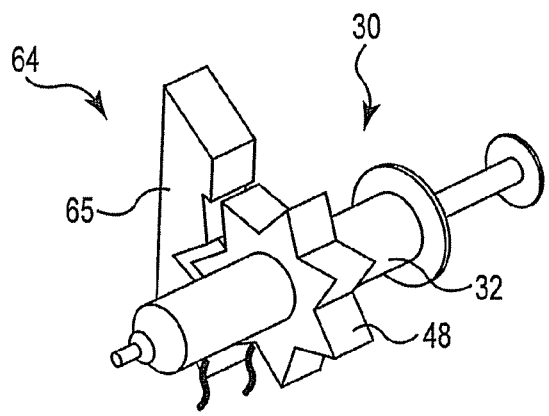

FIGS. 4A and 4B are perspective views illustrating the mating relationship between the geometric mating member 48 of the syringe 30 and the mating receptacle 64. Particularly, FIG. 4A is a perspective view that illustrates the geometric member 48 and corresponding receptacle 64 prior to mating, while FIG. 4B is a perspective view that illustrates the geometric member 48 and corresponding receptacle 64 after mating of the components. For ease of conveying the geometric differentiation aspect of the present invention, only the portion of the mating receptacle 64 that contains the mating surface 65 is depicted.

Figure 4C:
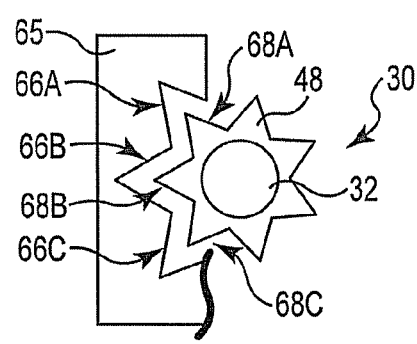

As illustrated in FIGS. 4A and 4B, the mating surface 65 of the mating receptacle 64 is structured to mate with the geometric mating member 48 on a single "side." Particularly, the mating surface 65 comprises a first mating groove 66A structured to mate with a first portion 68A of the geometric mating member 48, a second mating groove 66B structured to mate with a second portion 68B of the geometric mating member 48, and a third mating groove 66C structured to mate with a third portion 68C of the geometric mating member 48. FIG. 4C is a diagram illustrating an end view of the geometric mating member 48 upon mating with the mating surface 65 of the receptacle 64. Although FIG. 4C depicts a gap between the mating components, those skilled in the art will appreciate that such mating may bring the components together flush with no gap between them so that the geometrical "fit" would be more obvious to the user.

Figure 5:
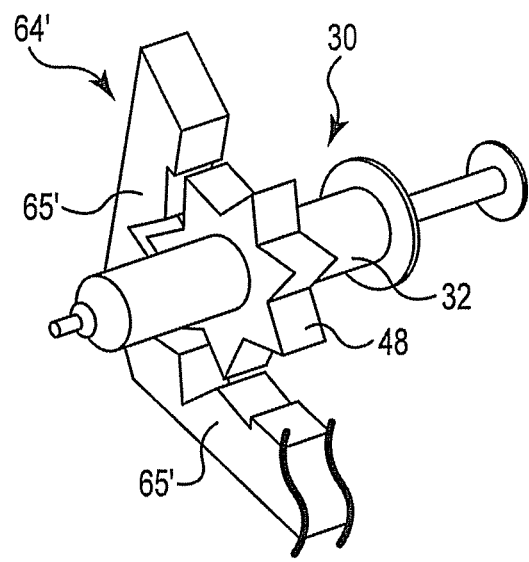
FIG. 5 is a perspective view illustrating the mating relationship between the geometric mating member of FIGS. 4A-4C and an exemplary alternative mating receptacle.

FIG. 5 is a perspective view illustrating the mating relationship between the syringe 30 and an exemplary alternative mating receptacle 64'. The mating receptacle 64' is generally similar to the mating receptacle 64 previously described and illustrated with regard to FIGS. 4A-4C, but further comprises a mating surface 65' that is structured to mate with the geometric mating member 48 on multiple "sides." Providing a mating receptacle that requires mating of the geometric mating member 48 on multiple sides may provide additional assurance that the proper syringe is being supplied to the delivery apparatus.

Figure 6:
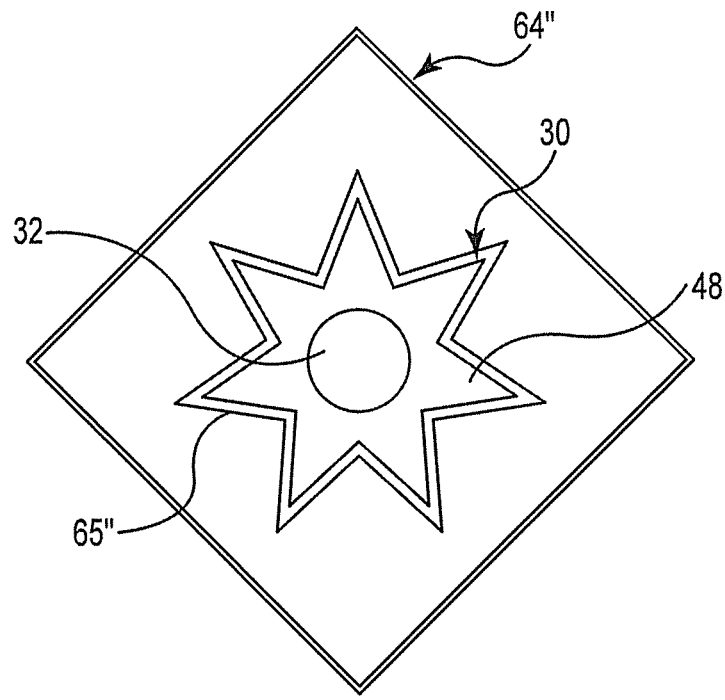
FIG. 6 is a perspective view illustrating the mating relationship between the geometric mating member of FIGS. 4A-4C and another exemplary alternative mating receptacle.

FIG. 6 is a diagram illustrating an end view of the syringe 30 in mating engagement with another exemplary alternative mating receptacle 64". The mating receptacle 64" is generally similar to the mating receptacles previously described and illustrated with regard to FIGS. 4A-4C and 5, but further comprises a mating surface 65" that is structured to surround the geometric mating member 48 on all "sides." As will be obvious to those skilled in the art, providing a mating receptacle that requires mating of the geometric mating member 48 on all sides may provide even further assurance that the proper syringe is being supplied to the delivery apparatus.

Those skilled in the art will appreciate that the geometric mating member on the medication container and the corresponding mating receptacle on the delivery apparatus may be designed to come together in one or more of many ways. For example, in one exemplary embodiment, the geometric mating member may be designed to slide into its mating receptacle from the top or bottom. In another exemplary embodiment, the geometric mating member may be designed for insertion from the side. Thus, the geometric mating member and corresponding mating receptacle may be designed for engagement in any suitable manner without departing from the intended scope of the present invention.

Now that one exemplary design for a geometric mating member and corresponding mating receptacle have been described in detail, numerous exemplary and non-limiting alternative designs will be described and illustrated. Particularly, FIGS. 7A-7I are diagrams illustrating exemplary differentiating geometries that may be used in accordance with the present invention. The circle in the middle of each diagram represents the outer circumference of the syringe barrel 32, with the geometric mating member being attached to the barrel as previously described. The geometric mating receptacles, which are attachable to a delivery apparatus, are provided to illustrate the mating relationship between the syringe and the delivery apparatus.

Figure 7A:
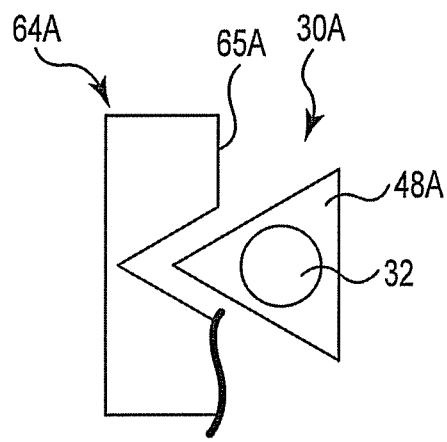

FIG. 7A is a diagram illustrating a syringe 30A having a first alternative geometric mating member 48A in accordance with the present invention. As shown in FIG. 7A, the geometric mating member 48A comprises a generally triangular-shaped geometrical differentiation member that is structured for mating with the mating surface 65A. The geometric mating member 48A is defined in part by three substantially identical planar surfaces. Thus, as will be appreciated by those skilled in the art, the geometric mating member 48A may be received by the corresponding geometric mating receptacle 64A in three different orientations.

Figure 7B:
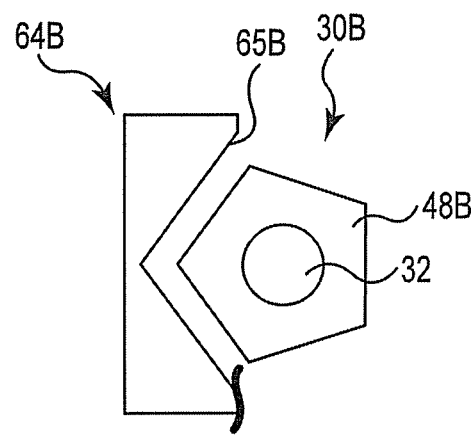

FIG. 7B is a diagram illustrating a syringe 30B having a second alternative geometric mating member 48B in accordance with the present invention. As shown in FIG. 7B, the geometric mating member 48B comprises a generally pentagonal-shaped geometrical differentiation member that is structured for mating with the mating surface 65B. The geometric mating member 48B is defined in part by five substantially identical planar surfaces. Thus, as will be appreciated by those skilled in the art, the geometric mating member 48B may be received by the corresponding geometric mating receptacle 64B in five different orientations.

Figure 7C:
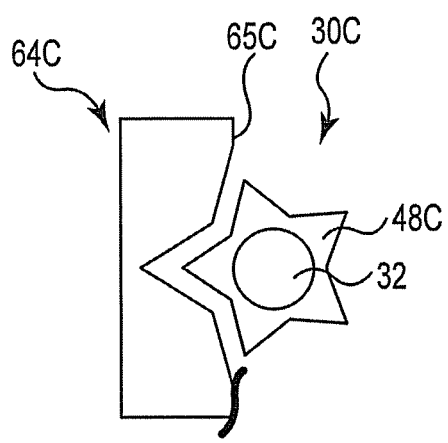

FIG. 7C is a diagram illustrating a syringe 30C having a third alternative geometric mating member 48C in accordance with the present invention. As shown in FIG. 7C, the geometric mating member 48C comprises a generally star-shaped geometrical differentiation member that is structured for mating with the mating surface 65C. The geometric mating member 48C is defined in part by ten substantially identical planar surfaces, and may be received by the corresponding geometric mating receptacle 64C in five different orientations as will be appreciated by those skilled in the art.

Figure 7D:
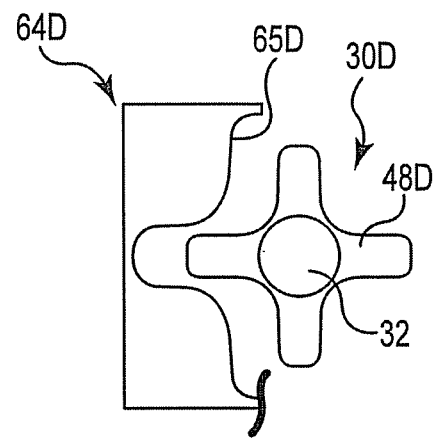

FIG. 7D is a diagram illustrating a syringe 30D having a fourth alternative geometric mating member 48D in accordance with the present invention. As shown in FIG. 7D, the geometric mating member 48D comprises a generally cross-shaped geometrical differentiation member that is structured for mating with the mating surface 65D. The four segments of the geometric mating member 48D are defined in part by both straight and curved surfaces, and the geometric mating member 48D may be received by the corresponding geometric mating receptacle 64D in four different orientations as will be appreciated by those skilled in the art.

FIG. 7E is a diagram illustrating a syringe 30E having a fifth alternative geometric mating member 48E in accordance with the present invention. As shown in FIG. 7E, the geometric mating member 48E comprises a generally oval-shaped geometrical differentiation member that is structured for mating with the mating surface 65E. The geometric mating member 48E is defined in part by a single continuous curved perimeter surface. The geometric mating member 48E is symmetrical, and thus may be received by the corresponding geometric mating receptacle 64E in two different orientations as will be appreciated by those skilled in the art.

FIG. 7F is a diagram illustrating a syringe 30F having a sixth alternative geometric mating member 48F in accordance with the present invention. As shown in FIG. 7F, the geometric mating member 48F comprises an irregularly-shaped geometrical differentiation member that is structured for mating with the mating surface 65F. The geometric mating member 48F is defined by both planar and curved surfaces, and may be received by the geometric mating receptacle 64F in only one orientation.

FIG. 7G is a diagram illustrating a syringe 30G having a seventh alternative geometric mating member 48G in accordance with the present invention. As shown in FIG. 7G, the geometric mating member 48G is different from those previously illustrated in that the mating member extends from only a portion of the syringe barrel 32. Particularly, the geometric mating member 48G is defined in part by a single protruding tab member that is receivable by the corresponding geometric mating receptacle 64G in only one orientation.

FIG. 7H is a diagram illustrating a syringe 30H having an eighth alternative geometric mating member 48H in accordance with the present invention. As shown in FIG. 7H, the geometric mating member 48H is different from those previously illustrated in that the mating member includes a recess or cut-out that is structured to receive a protrusion extending from the geometric mating receptacle 64H. Thus, the geometric mating receptacle 64H receives the geometric mating member 48H, which in turn receives a portion of the geometric mating receptacle 64H. As will be appreciated by those skilled in the art, the geometric mating member 48H may be received by the geometric mating receptacle 64H in only one orientation.

FIG. 7I is a diagram illustrating another alternative syringe 30I and corresponding geometric mating receptacle 64I in accordance with the present invention. As shown in FIG. 7I, the mating geometry of the syringe 30I is defined by the shape of the syringe barrel 32 itself and not by a protruding geometric mating member as in the previous embodiments. Thus, as will be appreciated by those skilled in the art, the geometry of the syringe barrel alone may serve as the differentiating geometry. Further, a circular-shaped barrel 32 is illustrated merely for purposes of example and not limitation, and any geometrically shaped barrel may be used without departing from the intended scope of the present invention.

In view of the foregoing non-limiting exemplary embodiments, those skilled in the art will appreciate that any suitable geometry that allows for differentiation between various containers may be used without departing from the intended scope of the present invention. Thus, the shape of the "differentiation geometry" may be polygonal or non-polygonal, regular or irregular, planar/straight or curved, concave or convex, etc., or any combination thereof.

As will also be appreciated by those skilled in the art, the container differentiation geometries may intentionally be made compatible with multiple receptacle geometries, providing the possibility to indicate one-to-many compatibility of treatment applications. Reciprocally, mating receptacles may be designed to accept multiple container geometries to indicate that any of a group of medications is acceptable in a given treatment application.

Figure 8:
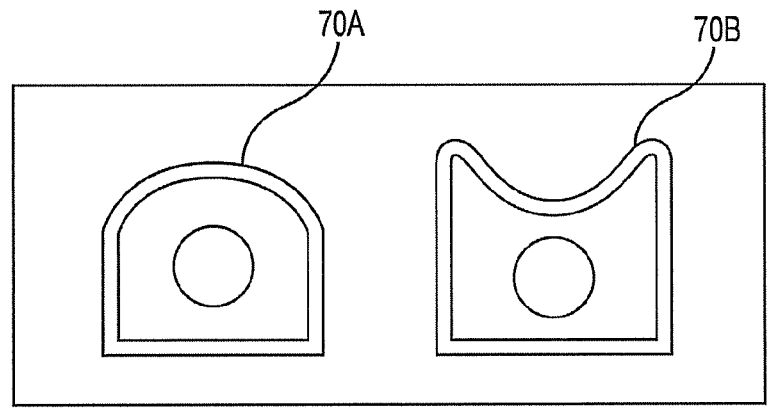
FIG. 8 is a diagram illustrating various differentiating geometries incorporated into a two-channel delivery environment.
Figure 9:
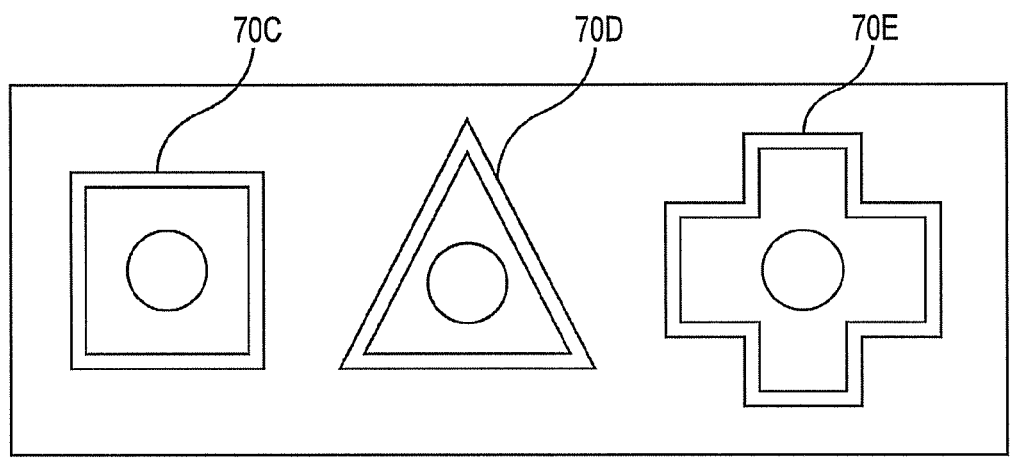
FIG. 9 is a diagram illustrating various differentiating geometries incorporated into a three-channel delivery environment.

When used in a multi-channel delivery environment, the employed geometries may be chosen to be most obviously incompatible in form with one another. For example, a two-channel environment might use a first geometric mating receptacle 70A with a convex shape and a second geometric mating receptacle 70B with a concave shape as illustrated in FIG. 8. A three-channel environment might use a first geometric mating receptacle 70C with a square shape, a second geometric mating receptacle 70D with a triangle shape, and a third geometric mating receptacle 70E with a "+" shape as illustrated in FIG. 9. Such designs facilitate differentiation by visual and tactile means as well as via part-counterpart mating on the delivery apparatus. Obviously, the above geometries are presented merely for purposes of example and not limitation. Thus, any suitable differentiating geometry may be used without departing from the intended scope of the present invention In addition to or in lieu of using geometric mating members and corresponding geometric mating receptacles as described above, various active or passive fixtures may be used to identify and differentiate medication containers. Such fixtures may be placed anywhere on the medication container and delivery apparatus to provide a further level of verification, and may be designed such that they line up only if the geometrical counterpart surfaces are mated properly. As will be described in further detail to follow, passive embodiments of such fixtures may include smaller geometrical counterparts such as patterned protrusions and receptacles. These fixtures may also serve as a tactile means for "feeling" when the components have been mated properly. Active embodiments of such fixtures may include electrical contacts that close a circuit or a reflective surface that allows optical detection when the components are mated together. Other active embodiments may utilize mechanical tension, magnetic fields, or some other measurable physical characteristic.

Figure 10:
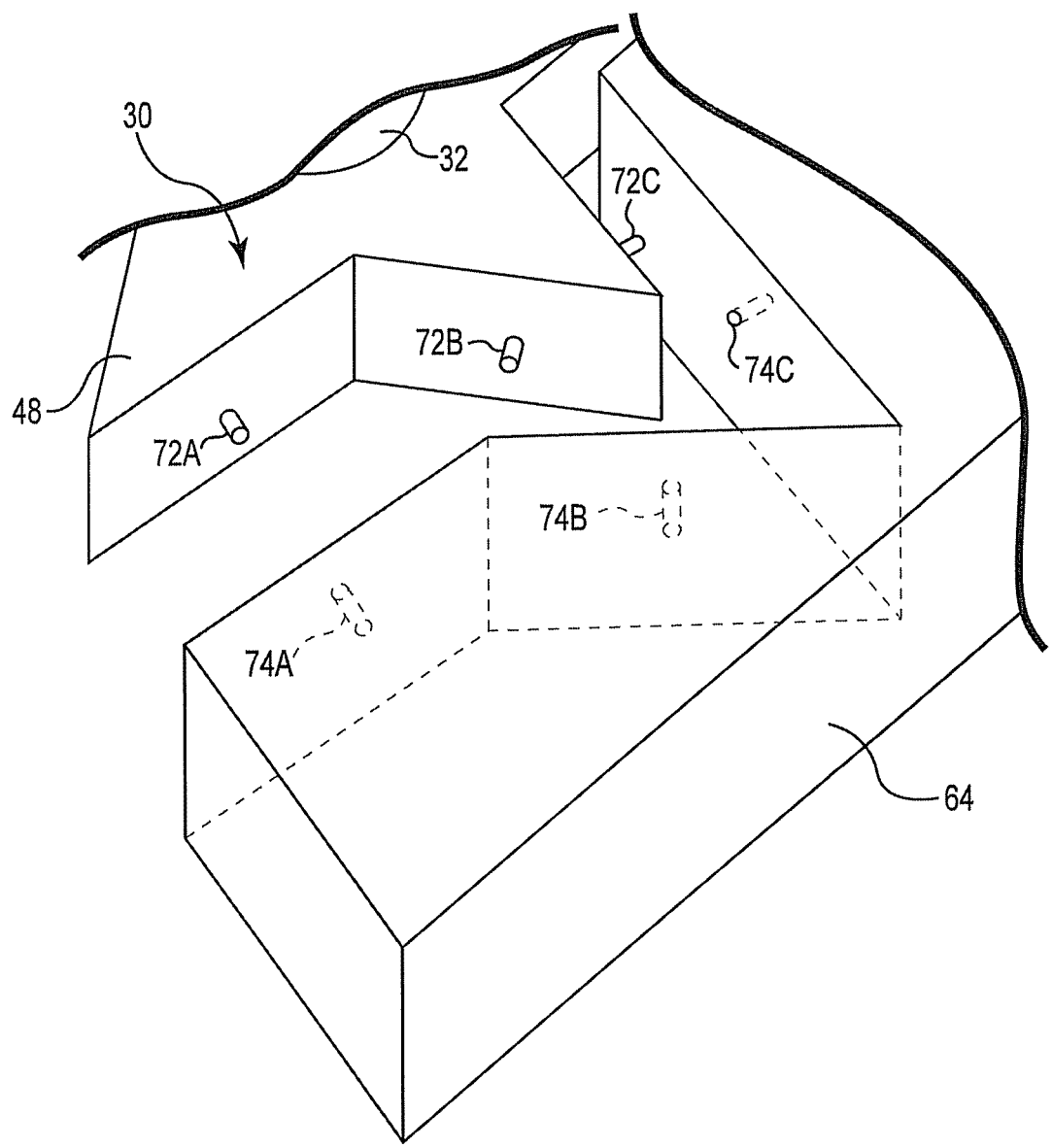
FIG. 10 is a partial perspective view of a syringe that incorporates both a geometric mating member and secondary mating fixtures for further verification of syringe compatibility.

FIG. 10 is a perspective view of the syringe 30 (with geometric mating member 48) and geometric mating receptacle 64 previously described with reference to FIGS. 4A-4C that further includes secondary mating fixtures in the form of geometrical protrusions 72A, 72B, and 72C designed to be received within corresponding mating receptacles 74A, 74B, and 74C. As will be appreciated by those skilled in the art, the secondary mating fixtures provide a second level of container verification. Particularly, the geometrical protrusions 72A, 72B, and 72C are receivable within the corresponding receptacles 74A, 74B, and 74C when the geometric mating member 48 is properly aligned with the mating receptacle 64. As will be appreciated by those skilled in the art, any number, shape, and location of secondary mating fixtures may be used without departing from the intended scope of the present invention.

Figure 11:
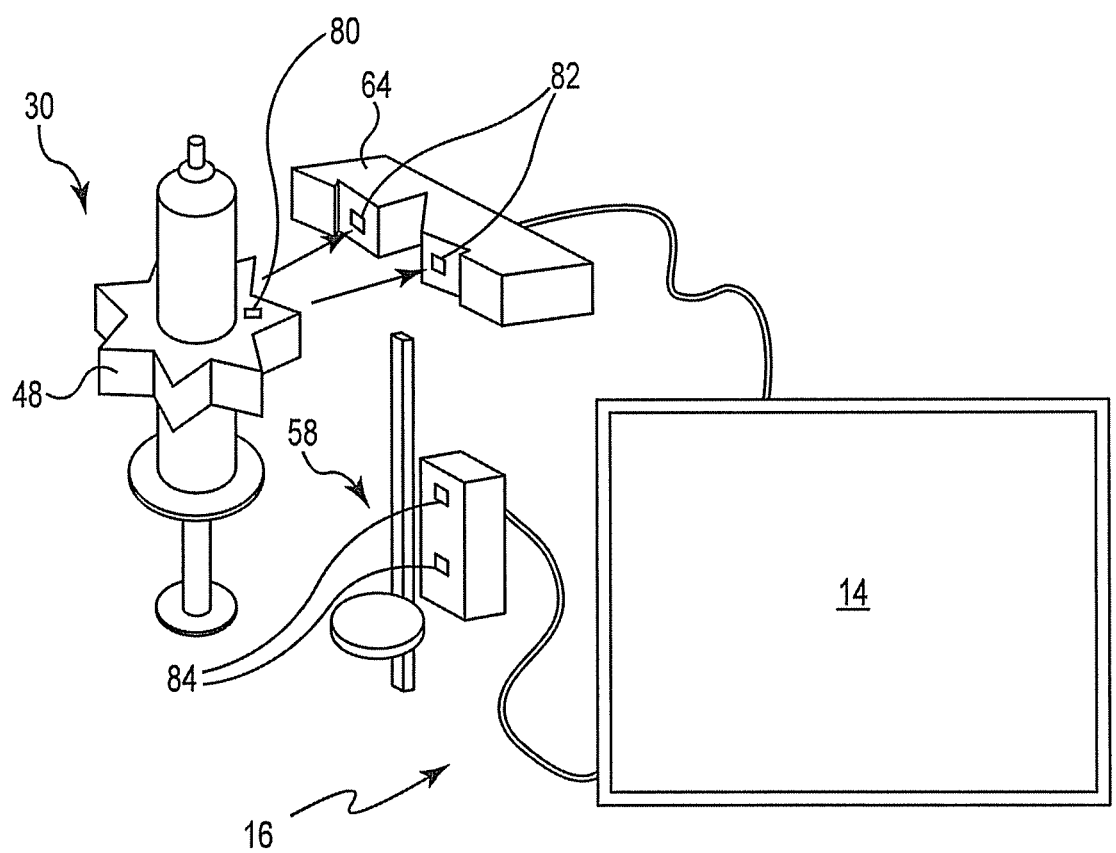
FIG. 11 is a diagram illustrating the use of active data fixtures for further verification of syringe compatibility.

As an alternative to using geometrical protrusions and receptacles as secondary mating fixtures, the syringe may utilize various types of active data fixtures as illustrated in FIG. 11. Particularly, as depicted in FIG. 11, the geometric mating member 48 includes a non-volatile memory chip 80 (such as an EEPROM chip) and one or more electrical contacts (not shown) that are designed for alignment with one or more corresponding electrical contacts 82 on the geometric mating receptacle 64 to transmit, communicate, or provide a signal, or to complete a circuit. Additionally, means for sensing the geometry or other physical characteristics of the syringe 30, such as one or more syringe geometry sensors 84, may be associated with the delivery apparatus. In one exemplary embodiment, the sensors 84 may be attached directly or indirectly to the pump motor 58 as depicted in FIG. 11. Further details regarding the function and operation of the data fixtures and sensors will be provided below.

Figure 12:
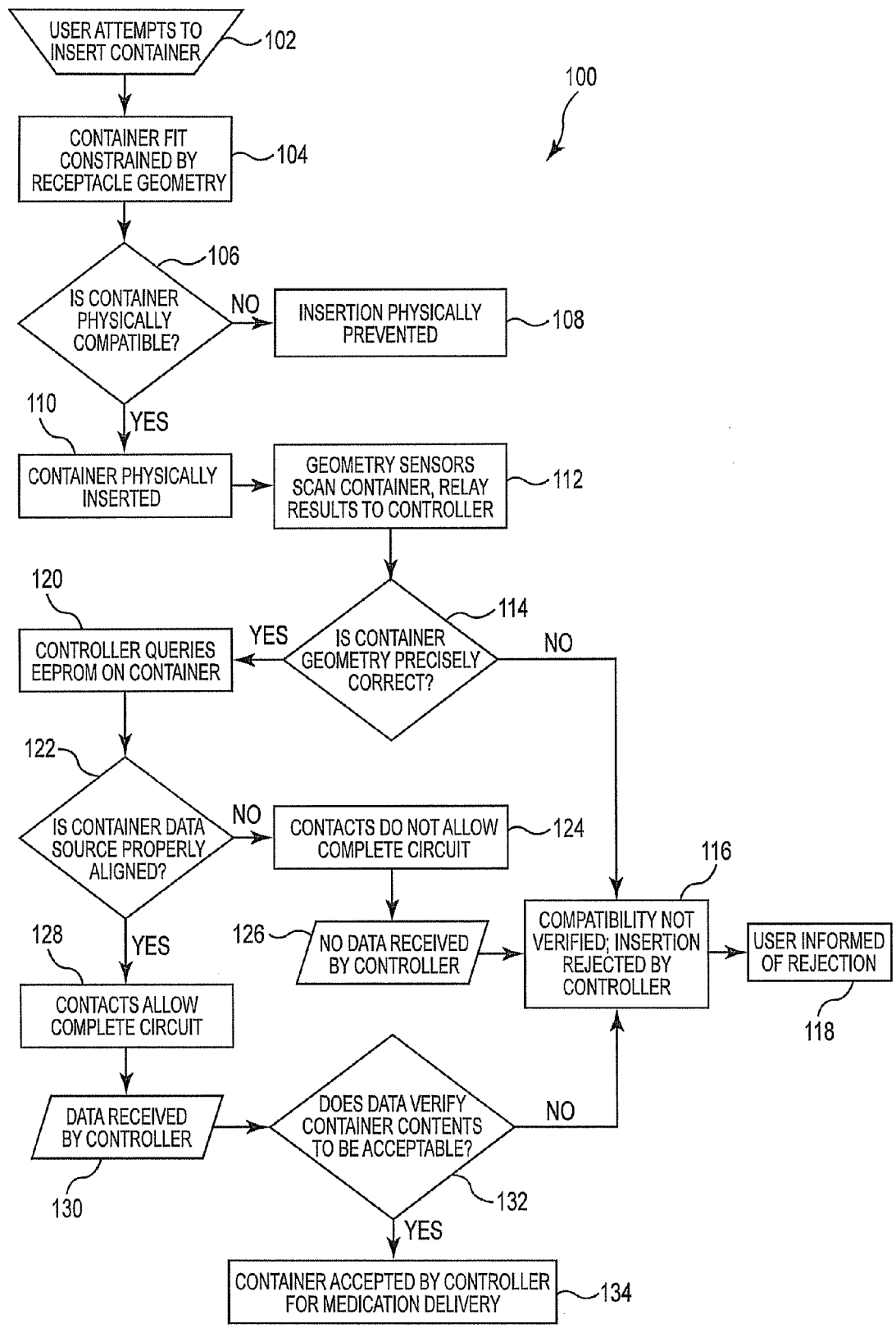
FIG. 12 is a flow diagram illustrating the steps in one exemplary medication container differentiation procedure in accordance with the present invention.

FIG. 12 is a flow diagram illustrating the steps in one exemplary medication container differentiation procedure 100 in accordance with the present invention. The differentiation procedure 100 begins at block 102 with the user attempting to insert a medication container into a container receptacle associated with the delivery apparatus. As indicated in block 104, the container is physically constrained by the geometry of the receptacle, and must therefore be able to fit within the physical boundaries imposed by the receptacle. For example, in one exemplary embodiment, the container must be inserted such that all geometrically differentiated parts on the container mate flush with their corresponding counterparts on the receptacle.

The differentiation procedure 100 continues at block 106 where the user determines whether the container is physically compatible with the receptacle. If the container does not meet the above criteria for physical insertion, the container is not able to be placed in the medication delivery apparatus, and the user has clear visual and tactile indication that the container is not intended for the current receptacle as indicated by block 108. However, if the container does meet the required criteria as indicated by block 110, an optional sensing means for sensing container presence, geometry, and/or other physical characteristics of the container may be activated to determine the precise physical nature of the inserted container as indicated by block 112. Any suitable sensing means may be employed including, but not limited to, sensors that verify the presence and position of certain physical characteristics including more detailed variations in container geometry and composition (such as the previously described "passive" fixtures), and/or sensors that identify the precise shape, dimensions, proportions, conductivity, hardness, weight, density, chemical composition, or other material or physical properties of the container. The sensing means may transmit the information to the controller for further processing.

Upon receipt of the information characterizing one or more properties of the container, the controller determines whether the container geometry is precisely correct at block 114. If the controller determines that the container is not of a type compatible with the current treatment application and/or delivery apparatus, insertion of the container is "rejected" as indicated by block 116. Whenever the controller rejects a container, the user may optionally be notified of the rejection as indicated by block 118, including a summary or detail of the reason for rejection. The notification may come via one or more suitable notification mechanisms such as, for example, visual cues including simple character display, colored or flashing lights, and/or a graphical user interface; audible cues such as a buzzer, generated audio sequences, and/or prerecorded sound clips; tactile cues such as haptic feedback and/or forcible physical ejection of the container; or any other suitable notification means as appreciated by those skilled in the art. Alternatively, if the controller determines that the container is compatible based upon the information characterizing one or more properties of the container, optional data fixture components on the container may be analyzed by one or more reader devices associated with the receptacle (such as by direct or indirect attachment thereto) as indicated by block 120. In one exemplary embodiment, the controller queries an EEPROM chip positioned on the container. However, any suitable data fixture component may be used without departing form the intended scope of the present invention.

Particularly, data fixtures include components that contain, generate, or otherwise indicate information which may be detected and received by a reader component, and subsequently relayed to the controller. The information may be transmitted as digital or analog signals. For example, the information may be as simple as a binary signal (e.g. the container is compatible if a certain signal is present, and incompatible if the signal is not present), or may implement a complete protocol for exchange of detailed information with the reader, including identification of the container and its contents. The data fixtures may be of a type requiring physical contact between the data fixture component on the container and its counterpart reader, such as electrical or optical contacts operable to transmit a simple signal or complex information. Alternatively, the data fixtures may be of a type that enables detection or transfer of information at some distance, such as via radio frequency or other electromagnetic means, optical barcode scanning, machine vision, or the like. Thus, the data fixtures may be passive, such as a reflective surface that returns a light source when found in the expected location, or active, such as a microprocessor located on the container, without departing from the intended scope of the present invention.

As will be appreciated by those skilled in the art, suitable technologies for data fixtures may comprise simple electrical means including completion of a circuit; more complex electrical means including electronic computer and memory devices; simple optical means including reflective surfaces; advanced optical means including barcode scanning and optical/laser information storage and transmission; visual means including machine vision and recognition; physical/mechanical means including means for interpreting peaks, valleys, and/or holes in a physical medium; chemical means including means for determining chemical reactivity and/or composition of a material; material analysis means including means for determining the charge of a substance or series thereof, or means for determining the vibration and/or resonance of a material; electromagnetic means such as radio frequency identification and communication including RFID, Bluetooth, or similar technology; and any other suitable technology that enables detection or identification of a container. Data fixture techniques may be applied to the entire container, a portion of the container, one or more objects affixed to the container (either temporarily or permanently), the packaging in which the container is delivered, the contents of the container including the contained medication, or the like.

It should be understood that the foregoing list of suitable technologies is presented merely for purposes of example and not limitation. Thus, the scope of the present invention is not limited by the specific technologies referenced.

Moving next to block 122, the controller determines whether the container data source is properly aligned. If the controller determines that the reader is unable to detect a compatible signal from or complete a circuit with its expected, corresponding data fixture as indicated by block 124, then no data will be received by the controller as indicated by block 126. Consequently, the controller determines that the container is not of a type compatible with the current treatment application and/or delivery apparatus at block 116, and the container insertion is rejected. Optionally, the user may be notified of the rejection at block 118 as discussed above. However, if the controller determines that the reader is able to detect a compatible signal from or complete a circuit with its expected, corresponding data fixture as indicated by block 128, then the reader obtains the information provided by the data fixture component as indicated by block 130 and relays the information to the controller. The controller then analyzes this information at block 132 to determine whether the container is of a type compatible with the current treatment application and/or delivery apparatus. This process is performed for all data fixtures expected by the controller and supported by the receptacle sensor set.

If, for any data fixture, the controller determines that the container data does not support compatibility with the current treatment application and/or delivery apparatus, insertion of the container is rejected as indicated by block 116. Optionally, the user may be notified of the rejection at block 118 as discussed above. However, if for all data fixtures the controller ascertains that the container data verifies its compatibility with the current treatment application and/or delivery apparatus, the container insertion is accepted as indicated by block 134. At this point, treatment using the contents of the medication container may proceed.

Although several exemplary steps were described with reference to the differentiation procedure 100, those skilled in the art will appreciate that the order and number of steps may be modified without departing from the intended scope of the present invention. Thus, the exemplary steps were provided merely for purposes of example and not limitation.

Figure 13:
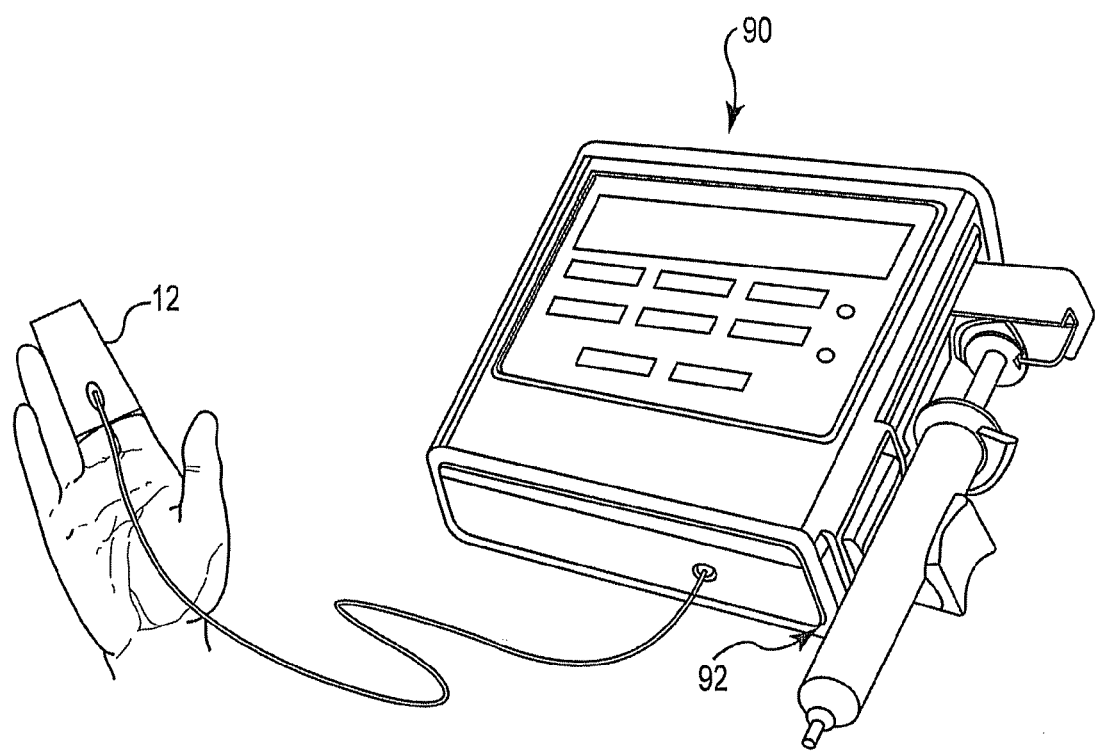
FIG. 13 is a perspective view of an exemplary delivery apparatus that is operable to differentiate/identify a syringe based solely upon information provided by geometry sensors and/or data fixtures.

Additionally, although the differentiation procedure 100 was described as including three "levels" of differentiation/identification based upon physical compatibility (e.g. block 106), information provided by geometry sensors (e.g. block 114), and information provided by data fixtures (e.g. block 122), providing all three levels of differentiation/identification is not necessary. Thus, any procedure that incorporates one or more of the foregoing compatibility checks (in any combination) is within the intended scope of the present invention. For example, FIG. 13 is a perspective view of an alternative delivery apparatus 90 that is operable to differentiate/identify a syringe 92 based solely upon information provided by geometry sensors and/or data fixtures. Thus, unlike the various embodiments of the syringe 30 previously described, the syringe 92 does not include a geometric mating member for mating engagement with a geometric mating receptacle. In view of the foregoing, it should be understood that the present invention encompasses the differentiation of medication containers with or without the use of physical geometrical differences in container geometry.

Figure 14:
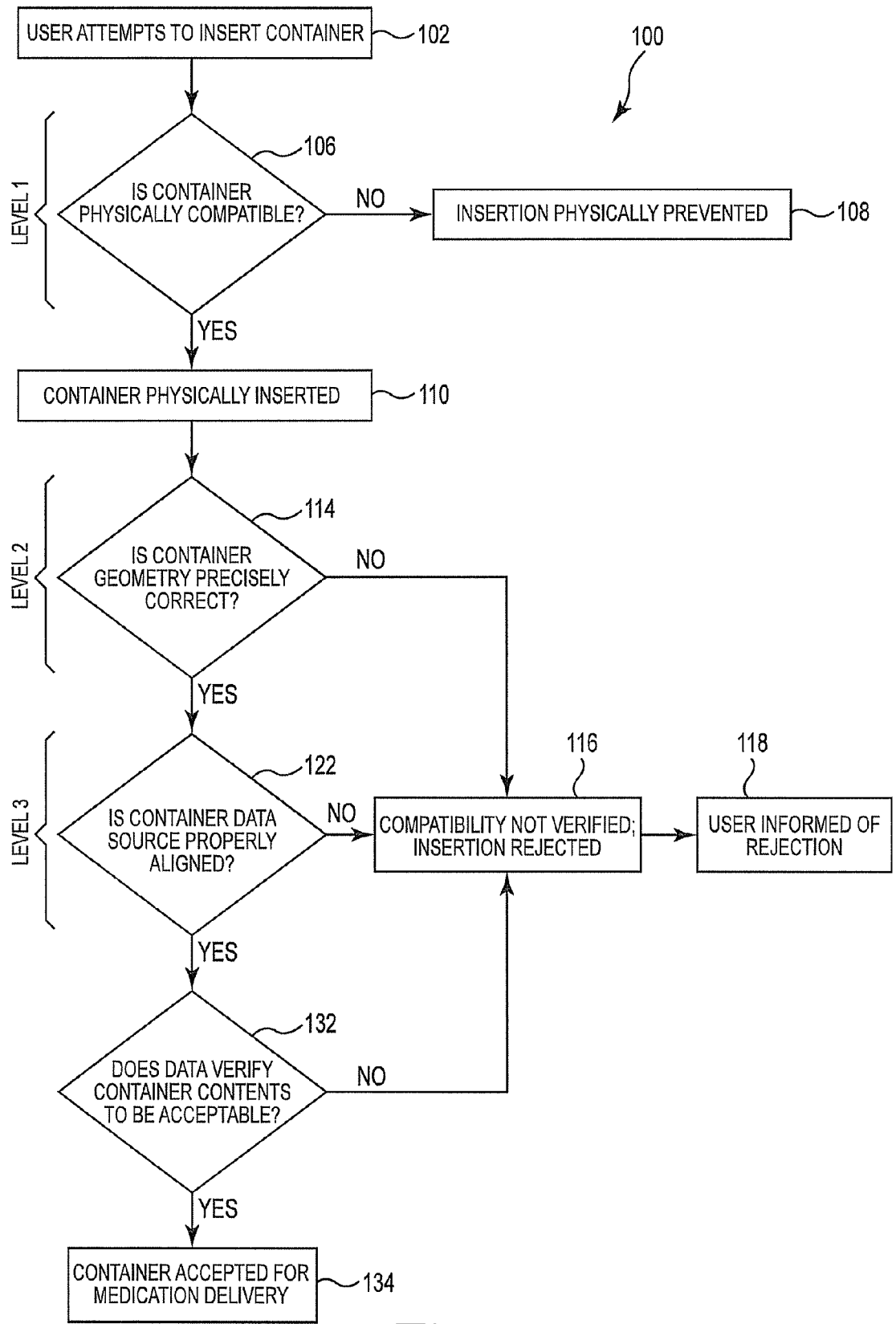
FIG. 14 is a condensed, version of the flow diagram of FIG. 12 illustrating several exemplary steps in the medication container differentiation procedure.

FIG. 14 is a condensed version of the flow diagram of FIG. 12 illustrating several exemplary steps in the medication container differentiation procedure 100 and identifying the three levels of differentiation/identification discussed above.

Figure 15:
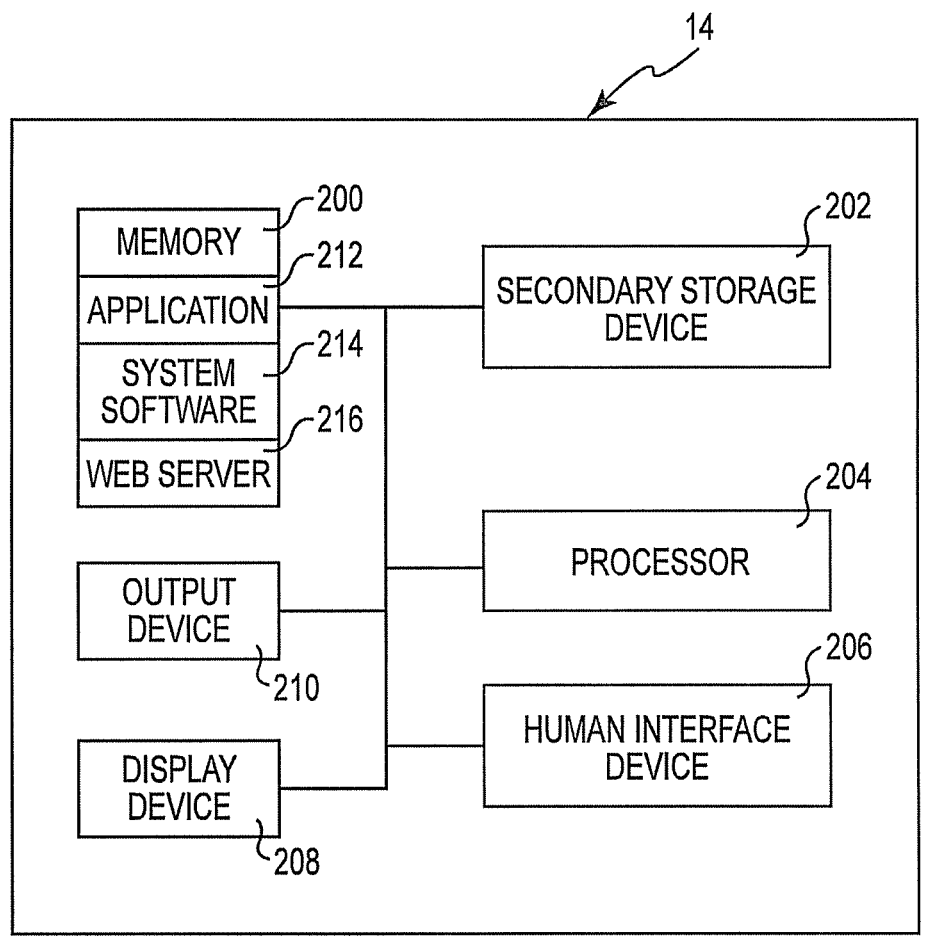
FIG. 15 is a block diagram illustrating exemplary components of a controller that may be used for processing information collected during the medication container differentiation procedure.

FIG. 15 is a block diagram illustrating exemplary components of the controller 14. As illustrated in FIG. 15, the controller 14 may include memory 200, a secondary storage device 202, a processor 204, a human interface device 206, a display device 208, and an output device 210. Memory 200 may include random access memory (RAM) or similar types of memory, and it may store one or more applications 212, including system software 214 and a web server 216, for execution by the processor 204. The secondary storage device 202 may include a hard disk drive, floppy disk drive, CD-ROM drive, or other suitable type of non-volatile data storage.

Information regarding medication containers may be stored in memory 200 or the secondary storage device 202. The processor 204 may execute the system software 214 and other applications 212 stored in memory 200 or the secondary storage device 202, or alternatively received from the Internet or other network as will be appreciated by those skilled in the art. The processor 204 may execute the system software 214 in order to provide the functions described in this specification including determining whether the container geometry is precisely correct based upon information from geometry sensors, determining whether container data fixture components are properly aligned to the corresponding readers, and verifying that the container contents are correct based upon information from the data fixtures. The human interface device 206 may include any device for entering information into the controller 14 including, but not limited to, a keyboard (such as the keyboard 52 of FIG. 3), mouse, cursor-control device, touch-screen, infrared, microphone, digital camera, video recorder, or any other suitable instrument or device. The display device 208 (such as the display 54 of FIG. 3) may include any type of device for presenting visual information such as, for example, a computer monitor or flat-screen display. The output device 210 may include any type of device for presenting information to a user, such as audo speakers or a printer.

The web server 216 may be used to provide access to information that is stored in memory 200 and/or on the secondary storage device 202, as well as to display such information remotely. The web server 216 allows users secure remote access to the system through which they can perform functions such as registering or programming rules for differentiating between medication containers, monitoring delivery of the appropriate medication to a patient, and the like. As appreciated by those skilled in the art, the web server 216 may allow access to a user running a web browser. Examples of web browsers include the Netscape Navigator program and the Microsoft Internet Explorer program. However, any web browser, co-browser, or other application capable of retrieving content from a network and displaying pages or screens may be used.

Examples of controllers 14 for interacting within the syringe differentiation system may include personal computers, laptop computers, notebook computers, palm top computers, network computers, Internet appliances, or any processor-controlled device capable of executing a web browser 216, system software 214, and any other type of application 212 stored in memory 200 and/or accessible via the secondary storage device 202. The controller 14 may be either integrated into or provided separate from the medication delivery apparatus as will be appreciated by those skilled in the art.

Although the present invention has been described with reference to preferred embodiments, workers skilled in the art will recognize that changes may be made in form and detail without departing from the spirit and scope of the invention.

What is claimed is:

1. A fluid delivery system comprising:
a fluid container having a chamber structured to hold a medication therein, the fluid container including a geometric mating member projecting radially outward therefrom, said geometric mating member or said fluid container including a data fixture thereon for sensing and transmitting information regarding one or more properties of said geometric mating member or said fluid container or both; a delivery device operable to control delivery of a fluid from the chamber of the fluid container, the delivery device including a geometric mating receptacle structured to physically mate with at least a portion of the geometric mating member of the fluid container to verify compatibility of the fluid container with the delivery device and communicate with said data fixture regarding said one or more properties of said geometric mating member or said fluid container or both; sensing means positioned on said delivery device for sensing and transmitting characteristics about said container; and a controller in communication with said sensing means and said data fixture, said controller having stored information regarding a physiological condition of a patient and a treatment plan, said controller operable to process said information regarding said one or more properties of said geometric mating member and accept or reject said information regarding said properties, and operable to accept or reject said information about said medication if it is incompatible with said physiological condition or said treatment plan, said controller including adaptive logic for stabilization of said physiological condition of the patient upon acceptance of said information about said medication.

2. The system of claim 1 wherein the geometric mating member is detachable from the fluid container.

3. The system of claim 1 wherein the geometric mating member and fluid container are formed as separate components that are permanently coupled to one another.

4. The system of claim 1 wherein the geometric mating member is formed integral with the fluid container.

5. The system of claim 1 wherein the geometric mating member defines an outer perimeter surface, and wherein the geometric mating receptacle is structured to mate with a portion of the outer perimeter surface.

6. The system of claim 5 wherein the geometric mating receptacle mates with and surrounds the entire outer perimeter surface of the geometric mating member.

7. The system of claim 1 wherein an outer perimeter surface of the geometric mating member defines a polygonal shape.

8. The system of claim 1 wherein an outer perimeter surface of the geometric mating member defines at least one curved portion.

9. The system of claim 1 wherein the fluid container is a syringe and wherein the geometric mating member extends radially outward from a barrel of the syringe.

10. The system of claim 9 wherein the delivery device is a syringe pump.

11. The system of claim 1 wherein the geometric mating member extends around the entire circumference of the fluid container.

12. The system of claim 1, further comprising one or more pairs of secondary mating fixtures associated with the geometric mating member and the geometric mating receptacle structured to further verify compatibility when the geometric mating member of the fluid container is mated with the geometric mating receptacle of the delivery device.

13. The system of claim 12 wherein the one or more pairs of secondary mating fixtures comprise geometrical protrusions and counterpart apertures that are structured to receive the protrusions upon alignment of the geometric mating member of the fluid container with the geometric mating receptacle of the delivery device.

14. The system of claim 12 wherein the one or more pairs of secondary mating fixtures comprise electrical contacts that complete an electrical circuit upon alignment of the geometric mating member of the fluid container with the geometric mating receptacle of the delivery device.

15. The fluid delivery system of claim 1 further comprising:
a pair of secondary mating fixtures including a first mating fixture associated with the fluid container and a second mating fixture associated with the delivery device;
said first and second mating fixtures structured to align with one another to further verify compatibility when the geometric mating member of the fluid container is mated with the geometric mating receptacle of the delivery device.

16. A method for verifying the compatibility of a fluid container with a fluid delivery device for delivery of a medication in accordance with a treatment plan comprising: providing a fluid container having a chamber structured to hold said medication therein, the fluid container including a geometric mating member extending from an outer surface thereof and a data fixture on said geometric mating member or container for sensing and transmitting information regarding one or more properties of said geometric mating member or said container or both; providing a delivery device operable to deliver said medication from the chamber of the fluid container, the delivery device including a geometric mating receptacle structured to physically mate with said geometric mating member, and communicate with said data fixture regarding said one or more properties of said geometric mating member, said container or both; providing sensing means positioned on said delivery device and operable for sensing and transmitting information about said container; verifying physical compatibility between the fluid container and the delivery device by mating at least a portion of the geometric mating member of the fluid container with the geometric mating receptacle of the delivery device; providing a controller in communication with said sensing means and said data fixture and operable to process information transmitted by said sensing means and said data fixture, said controller having stored information regarding a physiological condition of a patient and the treatment plan; accepting or rejecting said information transmitted by said sensing means and said data fixture regarding said one or more properties of said geometric mating member, said container or both; if said information transmitted by said sensing means or said data fixture regarding said one or more properties of said geometric mating member or said container, or both is accepted by said controller then accepting or rejecting said information about said medication and determining whether said medication is compatible with said treatment plan; and if said medication is compatible with said treatment plan causing said delivery device to deliver said medication to a patient according to said treatment plan.

17. The method of claim 16 wherein the step of verifying compatibility further comprises installing the fluid container within a delivery channel of the delivery device.

18. The method of claim 17 wherein an outer perimeter surface of the geometric mating member defines a polygonal shape.

19. The method of claim 16 wherein the fluid container is a syringe.

20. The method of claim 19 wherein the delivery device is a syringe pump.

21. The method of claim 16, further comprising the step of aligning a first mating fixture associated with the fluid container with a second mating fixture associated with the delivery device to further verify compatibility between the fluid container and the delivery device.

22. The method of claim 21 wherein the first mating fixture communicates information related to the fluid container to the second mating fixture.

\* \* \* \* \*